United States Patent [19]

North et al.

[11] Patent Number: 5,494,910
[45] Date of Patent: Feb. 27, 1996

[54] BENZOFURAN DERIVATIVES AS 5-HT₁-LIKE RECEPTOR ANTAGONISTS

[75] Inventors: Peter C. North; Sjoerd N. Wadman, both of Stevenage, Great Britain

[73] Assignee: Glaxo Group Limited, London, England

[21] Appl. No.: 406,981

[22] PCT Filed: Oct. 14, 1993

[86] PCT No.: PCT/EP93/02833

§ 371 Date: Mar. 31, 1995

§ 102(e) Date: Mar. 31, 1995

[87] PCT Pub. No.: WO94/08993

PCT Pub. Date: Apr. 28, 1994

[30] Foreign Application Priority Data

Oct. 16, 1992 [GB] United Kingdom ............ 9221761

[51] Int. Cl.⁶ .................. A61K 31/44; A61K 31/535; C07D 407/14; C07D 413/14
[52] U.S. Cl. .................. 514/233.5; 514/253; 514/318; 514/337; 544/131; 544/364; 546/193; 546/269
[58] Field of Search .................. 544/131, 364; 546/193, 269; 514/233.5

[56] References Cited

FOREIGN PATENT DOCUMENTS 0398413 11/1990 European Pat. Off. .
1670105 12/1970 Germany .

*Primary Examiner*—Robert W. Ramsuer
*Attorney, Agent, or Firm*—Bacon & Thomas

[57] ABSTRACT

This invention relates to benzofuran derivatives, to processes for their preparation, to pharmaceutical compositions containing them and to their medical use, in particular to compounds and compositions useful in the treatment of migraine. The compounds have the following general formula (I).

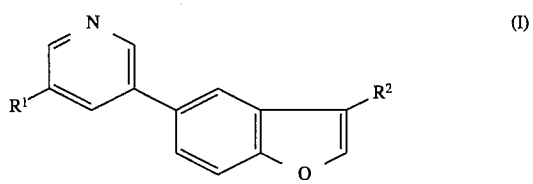

19 Claims, No Drawings

BENZOFURAN DERIVATIVES AS 5-HT₁-LIKE RECEPTOR ANTAGONISTS

This application is a 371 of PCT/EP93/02833 filed Oct. 14, 1993.

This invention relates to benzofuran derivatives, to processes for their preparation, to pharmaceutical compositions containing them and to their medical use, in particular to compounds and compositions of use in the treatment of migraine.

The invention thus provides compounds of formula (I)

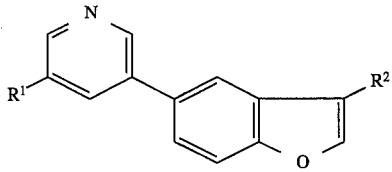

wherein $R^1$ is —$CH_2CONR^3R^4$;

$R^2$ is —$CH_2CH_2NR^5R^6$;

$R^3$ and $R^4$, together with the N-atom to which they are attached form a saturated 4- to 7-membered ring formula

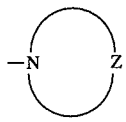

where

Z is a group of formula —$CR^7R^8$—, —O— or —$NR^9$—;

$R^5$ and $R^6$, which may be the same or different, are hydrogen or $C_{1-3}$alkyl;

$R^7$ and $R^8$, which may be the same or different, are hydrogen, hydroxy or $C_{1-3}$ alkoxy;

$R^9$ is —$SO_2R^{10}$, —$COR^{10}$ or —$COOR^{10}$;

$R^{10}$ is $C_{1-3}$alkyl;

and pharmaceutically acceptable salts and solvates (e.g. hydrates) thereof.

As used herein, an alkyl group may be a straight chain alkyl group, for example a methyl or ethyl group, or a branched chain alkyl group, for example an isopropyl group.

In a preferred class of compounds of formula (I) $R^3$ and $R^4$, together with the N-atom to which they are attached, form an azetidine, pyrrolidine, piperidine, hexamethyleneimine, piperazine or morpholine ring.

Typical values of $R^1$ include

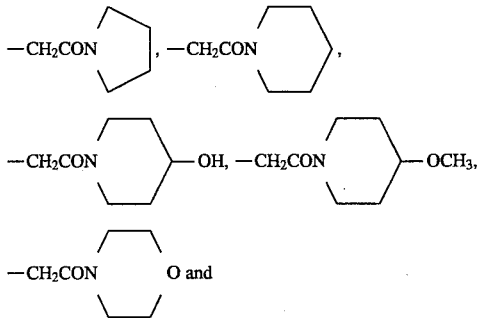

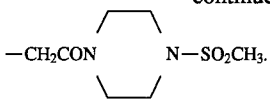

A particularly preferred class of compounds of formula (I) includes compounds wherein $R^5$ and $R^6$ are both methyl.

Preferred compounds according to the invention include:

1-[[5-[3-[2-(Dimethylamino)ethyl]-5-benzofuranyl]-3-pyridinyl]acetyl]piperidine;

1-[[5-[3-[2-(Dimethylamino)ethyl]-5-benzofuranyl]-3-pyridinyl]acetyl]pyrrolidine;

4-[[5-[3-[2-(Dimethylamino)ethyl]-5-benzofuranyl]-3-pyridinyl]acetyl]morpholine;

1-[[5-[3-[2-(Dimethylamino)ethyl]-5-benzofuranyl]-3-pyridinyl]acetyl]-4 -piperidinol;

1-[[5-[3-[2-(Dimethylamino)ethyl]-5-benzofuranyl]-3-pyridinyl]acetyl]-4 -methoxypiperidine;

1-[[5-[3-[2-(Dimethylamino)ethyl]-5-benzofuranyl]-3-pyridinyl]acetyl]-4 methylsulphonyl)piperazine;

1-[[5-[3-[2-(Dimethylamino)ethyl]-5-benzofuranyl]-3-pyridinyl]acetyl]-azetidine;

4-[[5-[3-[2-(Methylamino)ethyl]-5-benzofuranyl]-3-pyridinyl]acetyl]-acetyl] morpholine;

and pharmaceutically acceptable salts and solvates thereof.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Compounds of the invention may be isolated in association with solvent molecules by crystallisation from or evaporation of an appropriate solvent. Such solvates are included within the scope of the present invention.

References hereinafter to a compound according to the invention include both the compounds of formula (I) and their pharmaceutically acceptable salts and solvates.

The compounds of formula (I) are selective agonists at 5HT₁-like receptors and have selective vasoconstrictor activity. The selective 5HT₁-like receptor agonist activity and selective vasoconstrictor activity of the compounds of the invention has been demonstrated in vitro. In addition, compounds of the invention selectively constrict the carotid arterial bed of the anaesthetised dog whilst having negligible effect on blood pressure.

The compounds of the invention are indicated in the treatment of conditions susceptible to amelioration by agonist activity at 5HT₁-like receptors. In particular, compounds of the invention are useful in treating certain conditions associated with cephalic pain. In particular the compounds are useful in the treatment of migraine (including paediatric migraine), cluster headache, chronic paroxysmal hemicrania, headache associated with vascular disorders, tension-type headache, headache associated with substances of their withdrawal (e.g. drug withdrawal), trigeminal neuralgia, and headache associated with meningeal irritation, and in alleviating the symptoms associated therewith.

There is thus provided in a further aspect of the invention a compound of the invention or a salt thereof for use in therapy, in particular in human medicine. It will be appreciated that use in therapy embraces but is not necessarily limited to use of a compound of the invention or a salt thereof as an active therapeutic substance.

There is also provided as a further aspect of the invention the use of a compound of the invention in the preparation of a medicament for use in the treatment of conditions associated with cephalic pain, in particular migraine, cluster headache, chronic paroxysmal hemicrania, headache associated with vascular disorders, tension-type headache, headache associated with substances or their withdrawal (e.g. drug withdrawal), trigeminal neuralgia and headache associated with meningeal irritation.

In an alternative or further aspect there is provided a method for the treatment of a mammal, including man, comprising administration of an effective amount of a compound of the invention, in particular for the treatment of conditions associated with cephalic pain and in alleviating the symptoms associated therewith.

It will be appreciated by those skilled in the art that reference herein to treatment extends to prophylaxis as well as the treatment of established symptoms.

While it is possible that, for use in therapy, a compound of the invention may be administered as the raw chemical it is preferable to present the active ingredient as a pharmaceutical composition.

The invention thus further provides a pharmaceutical composition which comprises a compound of the invention together with one or more pharmaceutically acceptable carriers or excipients and, optionally, other therapeutic and/or prophylactic ingredients. The carrier(s) must be 'acceptable' in the sense of being compatible with the other ingredients of the formulation and not deleterious to the recipient thereof.

Pharmaceutical compositions include those suitable for oral, rectal, intranasal, topical, implant or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

For oral administration, the pharmaceutical compositions may take the form of, for example, tablets or capsules prepared by conventional means with pharmaceutically acceptable excipients such as binding agents (e.g. progelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch, croscarmellose sodium or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage from e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas. e.g. containing conventional suppository bases such as cocoa butter or other glyceride.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Any of the pharmaceutical compositions described above may be presented in a conventional manner associated with controlled release forms.

Preferably the pharmaceutical compositions according to the invention are suitable for oral, rectal or intranasal administration.

A convenient unit dose formulation contains the active ingredient in an amount of from 0.1 to 200 mg.

It will be appreciated that the amount of a compound of formula (I) required for use in treatment will vary not only with the particular compound selected, but also with the route of administration, the nature of the condition being treated and the age, weight and condition of the patient and will ultimately be at the discretion of the attendant physician or veterinarian. In general, however, a suitable dose will be in the range of from about 0.1 to about 200 mg per day, preferably in the range of 0.5 to 50 mg per day, most preferably in the range of 1 to 20 mg per day.

A suitable daily dose for use in prophylaxis will generally be in the range of 0.1 mg to 25 mg.

The desired dose may conveniently be presented in a single dose or as divided doses administered at appropriate intervals, for example as two, three, four or more sub-doses per day. The compound is conveniently administered in unit dosage form.

A proposed dose of the compounds of the invention for oral, rectal, intranasal, topical or parenteral administration to man (of approximately 70 kg bodyweight) for the treatment of migraine is 0.1 to 200 mg of the active ingredient per unit dose which could be administered, for example, 1 to 4 times per day.

For oral administration a unit dose will preferably contain from 2 to 200 mg of the active ingredient. A unit dose for parenteral administration will preferably contain 0.2 to 5 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 1 mg to 100 mg. Administration may be several times daily, for example from 2 to 8 times, giving for example 1, 2 or 3 doses each time.

Dosages of the compounds of the invention for rectal, intranasal or topical administration are similar to those for oral administration.

The compounds of the invention may, if desired, be administered in combination with one or more other therapeutic agents, such as analgesics, anti-inflammatory agents and anti-nauseants.

The combinations referred to above may conveniently be presented for use in the form of a pharmaceutical formulation and thus pharmaceutical formulations comprising a compound of formula (I) together with at least one other therapeutic agent, in particular an analgesic, anti-nauseant or anti-inflammatory agent, and a pharmaceutically acceptable carrier therefore comprise a further aspect of the invention.

When compounds of formula (I) are used in combination with other therapeutic agents, the compounds may be administered either sequentially or simultaneously by any convenient route.

When such combinations are employed the dose of each component of the combination will in general be that employed for each component when used alone.

Compounds of formula (I) and pharmaceutically acceptable salts and solvates (e.g. hydrates) thereof, may be prepared by methods known in the art for the preparation of analogous compounds. In particular the compounds of formula (I) may be prepared by the methods outlines below and which form a further aspect of the invention. In the following processes, $R^1$, $R^2$, $R^3$, $R^4$, $R^5$, $R^6$, $R^7$, $R^8$, $R^9$ and $R^{10}$ are as defined for formula (I) unless otherwise specified.

According to one general process (A) a compound of formula (I) may be prepared by coupling a compound of formula (II)

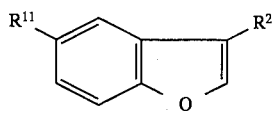

with a compound of formula (III)

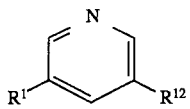

wherein one of $R^{11}$ and $R^{12}$ represents a readily displaceable atom or group, for example a halogen atom, preferably bromine, or a triflate group, and the other is a group of formula —$B(OH)_2$ or —$Sn(Alk)_3$ where Alk is alkyl, preferably $C_{1-3}$alkyl, e.g. methyl.

The reaction is effected in the presence of an appropriate catalyst such as palladium(O) or a palladium metal complex, e.g. tetrakis(triphenylphosphine)palladium(O) and, when one of $R^{11}$ and $R^{12}$ represents —$B(OH)_2$, a base such as an alkali metal carbonate, e.g. sodium carbonate. Conveniently the reaction is carried out in a suitable solvent such as water, 1,2-dimethoxyethane, N,N-dimethylformamide, tetrahydrofuran, dioxan, xylene, toluene or mixtures thereof, at a temperature of 0°–160° C., preferably at about 85° C.

Where they are not commercially available compounds of formula (II) and (III) may be prepared by methods known from the art.

Thus, for example, compounds of formula (II) or formula (III) wherein $R^{11}$ and $R^{12}$ are —$B(OH)_2$ may be prepared from the corresponding compounds wherein $R^{11}$ and $R^{12}$ represent a halogen atom, preferably bromine, via an organometallic intermediate, for example a lithiated or Grignard intermediate, by treatment with a trialkyl borate ester. Suitable reagents for lithiation include alkali metal alkyls, e.g. n-, sec-, or tert-butyl lithium. Suitable initiators of Grignard reactions are well know to those skilled in the art and include, for example, methyl magnesium chloride, ethyl magnesium chloride and ethyl magnesium bromide. The preparation of the organometallic intermediate is conveniently carrier out in an inert solvent, such as an ether, e.g. diethyl ether, tetrahydrofuran or dioxan, or a hydrocarbon, e.g. cyclohexane, benzene or toluene, at a temperature of —100°–50° C., preferably at about –78° C. for a lithiation reaction or at a temperature within the range of –10° C. up to the reflux temperature of the solvent employed, preferably at about 20° C. for a Grignard reaction. Suitable trialkyl borate esters include tri-methyl and tri-isopropylborate. Treatment of the organometallic intermediate with a trialkyl borate ester in conveniently carried out in an inert solvent such as an ether or a hydrocarbon as described above, at a temperature of –78°–100° C.

Compounds of formula (II) or (III) wherein $R^{11}$ and $R^{12}$ are —$Sn(Alk)_3$, may be prepared from the corresponding compounds wherein $R^{11}$ and $R^{12}$ represent a halogen atom, preferably a bromine, by treatment with a hexaalkyldistnnane, e.g. hexamethyldistannane, in the presence of a palladium metal complex, e.g. palladium tetrakis(triphenylphosphine). The reaction is conveniently carried out in an inert solvent, e.g. toluene or xylene, at a temperature of 0°–160°, preferably at about 140° C.

Intermediates of formula (II) wherein $R^{11}$ is a halogen atom may be prepared by reduction of a compound of formula (IV)

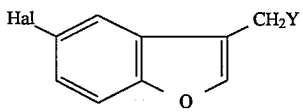 (IV)

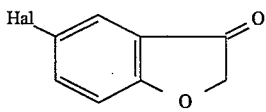 (VIII)

(wherein Y represents a nitrile group or the group $CONR^5R^6$) using a suitable reducing agent, e.g. lithium aluminium hydride, diisobutylaluminium hydride or borane, or hydrogen in the presence of a catalyst, in a suitable solvent. For the preparation of compounds of formula (II) wherein $R^5$ and $R^6$ do not both represent hydrogen atoms from compounds of formula (IV) wherein Y represents a nitrile group, the reduction should be carried out in the presence of an amine of formula $R^5_R{}^6NH$.

The reduction process may conveniently be carried out in the presence of hydrogen and a metal catalyst, for example, Raney nickel or a nobel metal catalyst such as palladium, platinum, platinum oxide or rhodium, which may be supported, for example, on charcoal. The reduction may be carried out in a solvent such as an alcohol, e.g. methanol or ethanol, an ether, e.g. dioxan, an ester, e.g. ethyl acetate, or an amide, e.g. dimethylformamide, and conveniently at a temperature of from $-10°-+50°$ C., preferably $20°-30°$ C. Suitable solvents for reduction using a metal hydride reducing agent include toluene, tetrahydrofuran, diethyl ether or dioxan, at a temperature of $-78°-100°$ C.

Intermediates of formula (III) wherein $R^{12}$ is a halogen atom may be prepared by reacting a compound of formula (V)

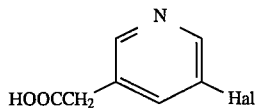 (V)

with an amine of formula (VI)

$HNR^3R^4$ (VI)

or an acid addition salt thereof in the presence of an amide coupling reagent such as diphenylphosphorylazide and a base such as triethylamine. Conveniently the reaction is carried out in a suitable solvent such as N,N-dimethylformamide at a temperature of $-78°-100°$ C. for example at about 20° C.

Intermediates of formula (II) wherein $R^1$ is

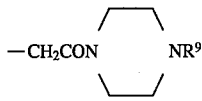

in which $R^9$ is $-SO_2R^{10}$ or $-COOR^{10}$ and $R^{12}$ is a halogen atom may be prepared by sulphonylation or acylation of the corresponding compound of formula (VII)

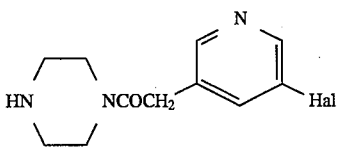 (VII)

using a suitable sulphonylating or acylating agent such as an acid halide, for example a sulphonyl chloride or a carboxylic acid chloride. The reaction is conveniently effected in a suitable solvent such as dichloromethane, in the presence of a suitable base such as triethylamine and at a temperature of $-78°-100°$ C., preferably at about 0° C.

Compounds of formula (IV) may be prepared by reaction of a compound of formula (VIII)

with a phosphorane of formula $Ph_3P=CHY$ in a suitable inert solvent such as xylene at a temperature of $0°-130°$ C., preferably at 130° C., or a phosphonate of formula $(R^{13}O)_2POCH_2Y$ (wherein $R^{13}$ is an alkyl group, e.g. an ethyl group) in the presence of a suitable base in a compatible solvent. Suitable combinations include: alkali metal hydrides, e.g. sodium hydride or potassium hydride, in an ether, e.g. diethyl ether, tetrahydrofuran or dioxan, or an amide, e.g. dimethylformamide; alkali metal alkoxides, e.g. sodium ethoxide, sodium methoxide or potassium tert-butoxide, in an alcohol, e.g. ethanol, methanol or tert-butanol; or alkyllithium, e.g. butyllithium, in an ether. Conveniently the reaction is carried out at a temperature of $-78°-50°$, preferably at $0°-23°$ C.

Compounds of formula (V), (VI) and (VIII) are known or may be prepared by processes known to those skilled in the art.

Compounds of formula (VII) may be prepared by processes analogous to those described for the preparation of compounds of formula (III) wherein $R^{12}$ represents a halogen atom.

According to another general process (B), a compound of formula (I) may be prepared by reaction of a compound of formula (IX)

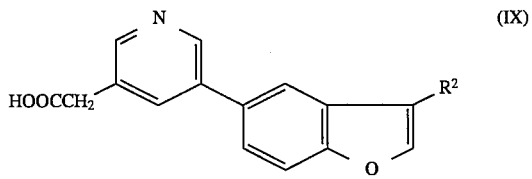 (IX)

with an amine of formula (VI) or an acid addition salt thereof, under conditions as described for the preparation of compounds of formula (III) from compounds of formula (V).

According to another general process (C), a compound of formula (I) according to the invention may be converted into another compound of the invention using conventional procedures.

Thus a compound of formula (I) wherein one or more of $R^5$ and $R^6$ represent a hydrogen atom, may be alkylated using conventional techniques. The reaction may be effected using a suitable alkylating agent such as an alkyl halide, an alkyl tosylate or a dialkylsulphate. The alkylation reaction may conveniently be carried out in an organic solvent such as an amide, e.g. dimethylformamide, or an ether, e.g. tetrahydrofuran, preferably in the presence of a base. Suitable bases include, for example, alkali metal hydrides, such as sodium hydride, alkali metal carbonates, such as sodium carbonate, or alkali metal alkoxides such as sodium or potassium methoxide, ethoxide or t-butoxide. The alkylation reaction is conveniently carrier out at a temperature of from $20°-100°$ C.

Alternatively, a compound of formula (I) wherein one or more of $R^5$ and $R^6$ represents a hydrogen atom may be converted to another compound of formula (I) by reductive alkylation. Reductive alkylation with an appropriate aldehyde or ketone may be effected using an alkaline earth metal borohydride or cyanoborohydride. The reaction may be effected in an aqueous or non-aqueous reaction medium, conveniently in an alcohol, e.g. methanol or ethanol or an ether, e.g. dioxan or tetrahydrofuran, optionally in the presence of water. The reaction may conveniently be carried out at a temperature in the range of 0°– 100° C., preferably 5°–50° C. Alternatively, the alkylation may be performed by heating a compound of formula (I) wherein one or more of $R^5$ and $R^6$ represents a hydrogen atom with the appropriate aldehyde or ketone such as formaldehyde in the presence of an acid such as formic acid at a temperature of 0°–150°, preferably at about 90° C.

According to another general process (D), a compound of formula (I) according to the invention, or a salt thereof may be prepared by subjecting a protected derivative of a compound of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W. Greene (John Wiley and Sons 1981).

Conventional amino protecting groups may include for example aralkyl groups, such as benzyl, diphenylmethyl or triphenylmethyl groups; and acyl groups such as N-benzyloxycarbonyl or t-butoxycarbonyl. Thus, compounds of general formula (I) wherein one or more of the groups $R^5$ and $R^6$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl, silicon protecting groups, such as trimethylsilyl or t-butyl dimethylsilyl groups, or as tetrahydropyran derivatives.

Removal of any protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation; silicon protecting groups may be removed, for example, by treatment with fluoride ion or by hydrolysis under acidic conditions; tetrahydropyran groups may be cleaved by hydrolysis under acidic conditions.

As will be appreciated, in any of the general process (A) to (C) described above it may be desirable or even necessary to protect any sensitive groups in the molecule as just described. Thus, a reaction step involving deprotection of a protected derivative of general formula (I) or a salt thereof may be carried out subsequent to any of the above described processes (A) to (C).

Thus, according to a further aspect of the invention, the following reactions may, if necessary and/or desired be carried out in any appropriate sequence subsequent to any of the processes (A) to (C):

(i) removal of any protecting groups; and
(ii) conversion of a compound of formula (I) or a salt thereof into a pharmaceutically acceptable salt or solvate thereof.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following Examples which should not be construed as constituting a limitation thereto. All temperatures are in °C. Ammonia ($NH_3$) or 0.88 $NH_3$ means aqueous ammonium hydroxide. DCM means dichloromethane. MeOH means methanol. EtOH means ethanol. THF means tetrahydrofuran. DME means dimethoxyethane. DMF means N,N-dimethylformamide. Dried means dried over anhydrous sodium sulphate (unless otherwise stated). Chromatography was performed on silica (Merck 9385 unless otherwise stated). IPA means iodoplatinic acid. T.l.c. means thin layer chromatography.

INTERMEDIATE 1

5-Bromo-3-benzofuranethanamine (i) 5-Bromo-3-(cyanomethyl)benzofuran

A suspension of 5-bromo-3-(2H)-benzofuranone (4.26 g) and cyanomethylene triphenylphosphorane (9.06 g) in dry xylene (100 ml) was heated at reflux for 24 h . A further quantity of the phosphorane (450 mg) was added and heating continued for a further period of 12 h. On cooling to ambient temperature the brown coloured suspension was evaporated to dryness in vacuo. Chromatography of the residue using dichloromethane:hexane (1:3) as eluant afforded a cream coloured product. Recrystallization (from ethanol) of the chromatographed material afforded the title compound as cream flakes, m.p. 120°.

T.l.c. $SiO_2$; DMC; Rf 0.73

(ii) 5-Bromo-3-benzofuranethanamine

To a stirred solution of the product of stage (i) (0.5 g) in dry THF (15 ml) at 0° was added a solution of borane in THF (3.2 ml of a 1M solution). The solution was warmed to room temperature and stirred for 3 h, a further quantity of borane in THF (3.2 ml of a 1M solution) was added and the solution stirred overnight. Methanol (5 ml) was added after cooling to 0°, followed by 2N hydrochloric acid (10 ml). The solution was refluxed for 1 h, cooled, the solvent removed in vacuo, dissolved in 2N hydrochloric acid (20 ml) and washed with ether (2×10 ml). The aqueous solution was neutralised with solid potassium hydroxide, extracted with dichloromethane (3×20 ml), dried and the solvent removed in vacuo. The crude material was purified by flash chromatography using dichloromethane:ethanol:ammonia (50:8:1) to yield the title compound as a pale yellow oil.

T.l.c. $SiO_2$; DCM:EtOH:0.88 $NH_3$ (50:8:1); Rf 0.48

INTERMEDIATE 2

5-Bromo-N,N-dimethyl-3-benzofuranethanamine (i) 5-Bromo-N,N-dimethyl-3benzofuranacetamide Dimethyl [2-(dimethylamino)-2-oxoethyl]phosphonate (5 g) was added to a stirred suspension of sodium hydride (1.02 g of a 60% dispersion in oil) in dry THF (100 ml) at 0° under nitrogen. After stirring for 15 minutes 5-bromo-3-(2H)-benzofuranone (5.0 g) in THF (20 ml) was added dropwise and stirred at room temperature for 3 h. Water (50 ml) was added and the mixture extracted with ethyl acetate (3×50 ml), dried and the solvent removed in vacuo. The crude material was purified by flash chromatography using 50% ethyl acetate/hexane as eluant to yield the title compound as a pale yellow solid m.p. 92°–94° C.

Analysis Found: C, 51,26; H, 4.28; N, 4.75.

$C_{12}H_{13}BrNO_2$ requires: C, 51.09; H, 4.29; N, 4.96.

(ii) 5-Bromo-N,N-dimethyl-3-benzofuranamine

Method A

To a solution of the product of stage (i) (3.3 g) in dry toluene (50 ml) at 0° was added diisobutylaluminium hydride (15 ml of a 1M solution in toluene). After 1 h a further quantity of diisobutylaluminium hydride solution (5 ml) was added. After 2 h the solution was poured into a stirred mixture of 2M sodium hydroxide solution (50 ml) and ether (100 ml). The solution was extracted with ether (3×50 ml), the combined extracts were washed with brine (50 ml) and dried. The solvent was removed in vacuo and the crude material purified by flash chromatography using dichloromethane:ethanol:ammonia (300:8:1→100:8:1) as eluant to yield the title compound as pale yellow oil.

T.l.c. $SiO_2$; DCM:EtOH:0.88 $NH_3$ (300:8:1); Rf 0.10

Method B

Intermediate 1 (1.20 g) was stirred with aqueous formaldehyde (1.22 ml). Two drops of formic acid were added and the mixture heated to 90° when $CO_2$ began to be evolved. Further formic acid (1.05 ml) was added dropwise over a period of 3 h. The reaction was heated for a further 2 h, diluted with dilute HCl (2N, 20 ml) and then evaporated to dryness. The residual oil was partitioned between aqueous sodium hydroxide (2N) and $CH_2Cl_2$. The aqueous phase was extracted with $CH_2Cl_2$ (×2) and the combined organic phases washed with water (×2), dried ($MgSO_4$) and evaporated to afford an oil. This was subjected to flash chromatography using $CH_2Cl_2$:EtOH:$NH_3$ (100:8:1) to give the product.

T.l.c. $SiO_2$; DCM:EtOH:0.88 $NH_3$ (300:8:1) Rf 0.35 identical to Method A.

INTERMEDIATE 3

3-[2-(Dimethylamino)ethyl]-5-benzofuranylboronic acid

Method A

To a stirred solution of Intermediate 2 (0.34 g) in dry THF (10 ml) at −78° was added sec-butyllithium (1.5 ml of a 1.3M solution in cyclohexane). After 30 minutes triisopropylborate (0.58 ml) was added and the solution allowed to warm to room temperature. The solution was stirred overnight, water (10 ml) added, the solvent removed in vacuo, ethanol (10 ml) added and the solvent again removed in vacuo to yield the product as a white foam which was used without further purification or characterisation.

Method B

A mixture of Intermediate 2 (10 g), methyl magnesium chloride (3M in tetrahydrofuran; 1 ml), and magnesium turnings (1 g) in dry tetrahydrofuran (50 ml) was stirred at 22° for 20 h to give a brown solution which was added over 1.5 h to a solution of trimethylborate (15 ml) and dry tetrahydrofuran (50 ml) maintained at −6° to −1°. After a further 0.5 h, water (50 ml) was added followed by isopropyl acetate (50 ml). The mixture was filtered, the cake washed with isopropyl acetate (2×20 ml) and the combined filtrates concentrated. 2M aqueous sodium hydroxide (10 ml) was added and the organic phase separated. The aqueous phase was extracted with isopropyl acetate (2×50 ml) and the combined organic phases back-extracted with 2M aqueous sodium hydroxide (1×30 ml, 2×20 ml). The pH of the combined aqueous extracts was adjusted to pH9 with concentrated hydrochloric acid before extracting with isopropyl acetate (3×50 ml). The combined organic extracts were dried ($MgSO_4$), filtered and concentrated to give the product as a pale brown foam.

T.l.c. $SiO_2$; DCM:EtOH:$NH_3$ (25:8:1); Rf=0.3

NMR: $\delta(CDCl_3)$ 2.55 (6H,s), 2.65 (2H,M), 2.85 (2H,m), 7.5 (1H,d), 7.8 (2H,m), 8.10 (1H,s)

INTERMEDIATE 4

4-[(5-Bromo-3-pyridinyl)acetyl]morpholine

A solution of 5-bromo-3-pyridine acetic acid (2.16 g) in anhydrous DMF (50 ml) containing triethylamine (2.58 ml) was stirred under $N_2$ and treated with morpholine (0.87 ml) and then diphenylphosphorylazide (3.03 ml). The straw coloured solution was stirred at room temperature for 18 h, diluted with water (10 ml) and stirred for 10 min. The mixture was rotary evaporated to remove volatile matter leaving behind a golden oil. This was diluted with water (100 ml) and 2N hydrochloric acid (50 ml), washed with ethyl acetate (2×75 ml), and basified to ca. pH10 with 2N sodium hydroxide (55 ml approx.). The basic aqueous solution was extracted with dichloromethane (4×100 ml) and the combined organic phases were washed with water (2×10 ml), dried ($MgSO_4$) and evaporated to give a white solid. This solid was washed with cyclohexane (200 ml), filtered, and dried to give the product as a white powder m.p. 122°–127°.

T.l.c. $SiO_2$ (DCM:EtOH:$NH_3$; 150:8:1) Rf 0.25, u.v./IPA

Assay Found: C, 46.1; H, 4.6; N, 9.7

$C_{11}H_{13}BrN_2O_2 \cdot 0.025H_2O$ requires: C, 46.2; H, 4.6; N, 9.8

Water Assay Found: 0.15% w/w $H_2O$.

Theory (0.025 $H_2O$):0.16%

INTERMEDIATE 5

Method A

4-[[5-(Trimethylstannyl)-3-pyridinyl]acetyl]morpholine

A degassed mixture of intermediate 4 (9.30 g), hexamethyldistannane (13.5 ml), palladium tetrakis(triphenylphosphine) (400 mg), and xylene (400 ml) was heated at reflux under a nitrogen atmosphere with string for 44 h. During this time, additional palladium tetrakis(triphenylphosphine) was added after 3 h (300 mg), 20 h (300 mg), and 24 h (100 mg). The mixture was evaporated, and the dark residual oil was purified by column chromatography over silica gel eluting with a mixture of 5% ammoniacal methanol and dichloromethane (5:95) to give the stannane as a colourless oil.

T.l.c. SiO$_2$:5% NH$_3$ in MeOH:DCM (5:95); Rf=0.35

NMR:δ(CDCl$_3$) 8.52 (1H,d), 8.39 (1H,d), 7.68 (1H,t), 3.68 (6H,d), 3.6–3.5 (4H,2×m), 0.30 (9H,s)

Method B

A degassed mixture of Intermediate 4 (52.8 g), hexamethyldistannane (81 g), palladium tetrakis(triphenylphosphine) (1 g), and xylenes (1.6 L) was heated at 100°–110°, under a nitrogen atmosphere with stirring for 20 hours. The cooled reaction mixture was clarified and evaporated to give a dark residual oil, which was purified by column chromatography (silica gel) eluting with a mixture of 10% ammoniacal methanol and dichloromethane (1:24) to give the stannane as an oil which crystallised on standing.

T.l.c. SiO$_2$:DCM:MeOH:NH$_3$ (490:10:1); Rf=0.15.

NMR: identical to Method A.

INTERMEDIATE 6

3-[2-(Dimethylamino)ethyl]benzofuran-5-yl trifluoromethanesulphonate i) (E)-N,N,N',N'-Tetramethyl-1-butene-1,4-diamine

Method A

To a slurry of 3-chloro-N,N-dimethylpropanamine hydrochloride (100 g) in toluene (50 ml) was added 2M aqueous sodium hydroxide (150 ml). The aqueous phase was extracted with toluene (2×50 ml) and the combined organic phases dried (MgSO$_4$) and filtered. A portion was further dried azeotropically and then added over 0.5 h to a slurry of magnesium turnings (5.7 g) in dry tetrahydrofuran (150 ml) heated at reflux. After 2 h, N,N-dimethylformamide (17.5 ml) was added over 0.5 h. Reflux was maintained for a further 2 h before the mixture was cooled to room temperature, filtered, concentrated and the residue purified by short path distillation to give the product as a clear colourless oil.

Method B

A mixture of (E)-N,N,N',N'-tetramethyl-2-butene-1,4-diamine (5 g) and potassium tert-butoxide (3.9 g) in tetrahydro-1,3-dimethyl-2(1H)-pyrimidinone (10 ml) was heated at 100° for 24 h. The mixture was purified by short path distillation to give the product as a clear colourless oil.

NMR: δ(CDCl$_3$) 2.1–2.4 (10H,m), 2.55 (6H,s), 4.15 (1H, dt), 5.95 (1H,d)

Boiling point: 100°–125° at 3 mmHg ii) 2-(Dimethylamino)-3-[2-(dimethylamino)ethyl]-2,3-dihydro-5-benzofuranol p-Benzoquinone (2.8 g) was added inone portion to a stirred solution of the intermediate from step (i) (3.72 g) in toluene (20 ml). After 16 h, the precipitate was isolated by filtration, washed with toluene (2×5 ml) and air dried to give the product as a light brown powder.

T.l.c. SiO$_2$; DCM:EtOH:NH$_3$ (25:8:1); Rf=0.1–0.4

NMR: δ(CDCl$_3$) 1.85 (2H,m), 2.1–2.5 (14H,m), 3.15 (1H,dt), 5.05 (1H,d), 6.5–6.7 (3H,m).

iii) 5-Hydroxy-N,N-dimethyl-3-benzofuranethanamine

A solution of the intermediate from step (ii) (4.1 g) in 5M aqueous hydrochloric acid (40 ml) was heated at reflux for 1.5 h, cooled to 20°, washed with tertiary butyl methyl ether (3×40 ml) and then washed with ethyl acetate (3×40 ml). The pH was adjusted to pH8 with aqueous sodium hydroxide and the solution extracted with ethyl acetate (4×40 ml). The combined extracts were dried (MgSO$_4$), filtered and concentrated to give the product as a brown oil.

T.l.c. SiO$_2$; DCM:EtOH:NH$_3$ (50:8:1); Rf=0.3

NMR: δ(CDCl$_3$) 2.40 (6H,s), 2.75 (2H,m), 2.85 (2H,m), 6.8 (2H,m), 7.30 (1H,d), 7.40 (1H,s).

iv) 3-[2-(Dimethylamino)ethyl]benzofuran-5-yl trifluoromethanesulphonate

A solution of trifluoromethanesulphonic acid anhydride (3.1 ml) in cyclohexane (7.5 ml) was added over 1 h to a stirred solution of the intermediate from step (iii) (3.8 g) and triethylamine (2.5 ml) in ethyl acetate (38 ml) maintained at 0°–5°. A further quantity (3 ml) of a solution of trifluoromethanesulphonic acid anhydride (1 ml) in cyclohexane (4 ml) was added over 1 h. The solution was concentrated and the residual gum was purified by chromatography over silica gel eluting with a mixture of DCM, EtOH, and NH$_3$ (150:8:1) to give the product as a pale brown oil.

T.l.c. SiO$_2$; DCM:EtOH:NH$_3$ (150:8:1); Rf=0.4

NMR: δ(CDCl$_3$) 2.55 (6H,s), 2.85 (2H,m), 2.95 (2H,m), 7.2 (1H,dd), 7.50 (1H,s), 7.55 (1H,d), 7.65 (1H, br.s)

EXAMPLE 1

1-[[5-[3-[2-(Dimethylamino)ethyl]-5-benzofuranyl]-3-pyridinyl]acetyl]piperidine oxalate (1:1)

a) 1-[(5-Bromo-3-pyridinyl)acetyl]piperidine

A mixture of 5-bromo-3-pyridine acetic acid (0.5 g), piperidine (247 μl), triethylamine (966 μl), diphenylphosphoryl azide (746 μl), and DMF (10 ml) was stirred at +23° for 66 h. The mixture was evaporated, and the residual gum was purified by column chromatography over silica gel eluting with a mixture of 5% ammoniacal methanol and dichloromethane (3:97) to give the product as a colourless oil.

T.l.c. SiO$_2$; 5% NH$_3$ in MeOH:DCM (3:97); Rf=0.60

M.S. Found MH$^+$=283, 285; Required MH$^+$=283, 285

NMR: δ(CDCl$_3$) 8.58 (1H,d), 8.39 (1H,d), 7.80 (1H,t), 3.70 (2H,s), 3.59 (2H,m), 3.42 (2H,m), 1.7–1.45 (6H,m).

b) 1-[[5-[3-[2-(Dimethylamino)ethyl]-5-benzofuranyl]-3-pyridinyl]acetyl] piperidine oxalate (1:1)

A degassed mixture of the intermediate from step (a) (360 mg), Intermediate 3 (296 mg), palladium tetrakis(triphenylphosphine) (116 mg), 2N aq. sodium carbonate (6.5 ml), and 1,2-dimethyoxyethane (24 ml) was heated in a nitrogen atmosphere at reflux with stirring for 4 h. The mixture was treated with additional 2N aq. sodium carbonate (20 ml), extracted with ethyl acetate (3×20 ml), and the combined organic extracts were washed with brine (1×20 ml), dried, and evaporated to leave an oil. The oil was purified by column chromatography over silica gel eluting with a mixture of 5% ammoniacal methanol and dichloromethane (8.92) to give a colourless gum. The gum was dissolved in ethanol (4 ml) containing oxalic acid (105 mg) and diethyl ether (10 ml) was added to precipitate the product as a hydroscopic white solid, m.p. 158°–160°.

T.l.c. $SiO_2$:5% $NH_3$ in MeOH: DCM (8.92); Rf=0.30 (free base)

MS: Found $MH^+$=392; Required $MH^+$=392

NMR: δ($CDCl_3$) 8.84 (1H,d), 8.42 (1H,d), 8.08 (1H,d), 8.0 (1H,s), 7.96 (1H 7.74 (1H,d), 7.65 (1H,dd), 3.85 (2H,s), 3.58–3.38 (6H,m), 3.14 (2H ½ AA'BB'), 2.86 (6H,s), 1.65–1.38 (6H,m).

EXAMPLE 2

1-[[5-[3-[2-(Dimethylamino)ethyl]-5-benzofuranyl]-3-pyridinyl]acetyl]pyrrolidine dihydrochloride a) 5-[3-[2-(Dimethylamino)ethyl]-5-benzofuranyl]-3-pyridineacetic acid 5-Bromo-3-pyridine acetic acid (936 mg), Intermediate 3 (999 mg), and aqueous 2N sodium carbonate (18 ml) in DMF (100 ml) were stirred under nitrogen whilst nitrogen was bubbled through the mixture for 1 min. Tetrakis(triphenylphosphine)palladium (O) (208 mg) was added and the mixture stirred at reflux for 7 h. The cooled reaction mixture was evaporated. Aqueous 2N sodium carbonate (10 ml) was added and the mixture adsorbed onto silica gel (Merck 7734). The resulting silica was then applied to a flash column of silica gel (6 cm wide column) and eluted with dichloromethane:ethanol:0.88 ammonia (89:10:1→50:45:5) to give the product as a cream foam.

NMR: δ(DMSO-$d^6$) 8.85 (1H,d), 8.47 (1H,d), 8.05 (2H, m), 7.92 (1H,s), 7.70, 7.65 (2H,d+dd), 3.75 (2H,s), 3.03–2.80 (4H,AA'BB'), 2.45 (6H,s).

b) 1-[[5-[3-[2-(Dimethylamino)ethyl]-5-benzofuranyl]-3-pyridinyl]acetyl]pyrrolidine dichloride Diphenylphosphorylazide (1.40 g) was added dropwise at below −5°, under nitrogen, to a stirred solution of the intermediate from step (a) (554 mg), pyrrolidine (182 mg) and triethylamine (1.43 ml) in DMF (35 ml). The mixture was stirred for 20 h, during which time the temperature was allowed to rise to +23°. The reaction mixture was evaporated and the residue applied to a flash column of silica gel (100 g). Elution with dichloromethane:ethanol:0.88 ammonia (200:8:1;43 100:8:1) gave a brown gum which was dissolved in ethanol and treated with 1M ethereal hydrogen chloride (1.5 ml). Evaporation gave the product as a white foam m.p. 118°–125°.

T.l.c. $SiO_2$; $CH_2Cl_2$:EtOH:0.88 $NH_3$, (100:8:1); Rf 0.26; u.v.

NMR: δ(DMSO-$d_6$) 10.75 (1H,brs), 9.27 (1H,brs), 8.82 (1H,brs), 8.75 (1H,brs), 8.45 (1H,brs), 8.06 (1H,brs), 7.9–7.78 (2H,m), 4.0 (2H,s), 3.7–3.18 (8H,2xt+ 2xm), 2.88 (6H,d), 2.03–1.78 (4H,2xm).

EXAMPLE 3

4-[[5-[3-[2-(Dimethylamino)ethyl]-5-benzofuranyl]-3-pyridinyl]acetyl]morpholine A mixture of Intermediate 3 (1.0 g), Intermediate 4 (1.21 g) and palladium tetrakis(triphenylphosphine) (0.48 g) was mixed with DMF (200 ml) and 8% aqueous sodium bicarbonate solution (50 ml) and stirred under nitrogen at 103° for 19 h. The volatile material (DMF/$H_2O$) was removed by rotary evaporation and the residual grey solid was mixed with aqueous 8% aq. $NaHCO_3$ solution (100 ml)/water (50 ml) and extracted with $CH_2Cl_2$ (4×100 ml). The organic extracts were washed with water, extracted with 2N hydrochloric acid (3×5 ml) and the combined acidic extracts were washed with $CH_2Cl_2$ (2×50 ml), before basifying with solid (KOH). The resulting suspension was extracted with $CH_2Cl_2$ (4×100 ml), washed with water (200 ml), dried ($MgSO_4$) and evaporated to give the free base of the product as an almost colourless gum.

This gum was purified by flash chromatography eluting with DCM:EtOH:$NH_3$ (100:8:1–50:8:1) to give the product as a pale brown gum.

T.l.c. $SiO_2$; DCM:EtOH:0.88 $NH_3$ (50:8:1); Rf 0.75

The product (1.035 g) in warm alcohol (5 ml) was treated with a warm solution of oxalic acid (0.257 g) in alcohol (5 ml). The resultant solution was rotary evaporated to dryness to give the oxalate salt as an off-white foam m.p. 82°–90° (softens at 70°)

T.l.c. $SiO_2$; DCM:EtOH:0.88 $NH_3$ (50:8:1); Rf 0.75

Assay Found: C,38.8; H,6.7; N7.8.

$C_{23}H_{27}N_3O_3 \cdot C_2H_2O_4 \cdot 1.5H_2O$ requires: C, 58.8; H, 6.3; N, 8.2.

EXAMPLE 4

1-[[5-[3-[2-(Dimethylamino)ethyl]-5-benzofuranyl]-3-pyridinyl]acetyl]-4-piperidinol dihydrochloride a) 1[(5-Bromo-3-pyridinyl)acetyl]-4-piperidinol A mixture of 5-bromo-3-pyridine acetic acid (1.00 g), 4-hydroxypiperidine (468 mg), triethylamine (2.6 ml), diphenylphosphoryl azide (2.00 ml), and DMF (60 ml) was stirred at +23° for 18 h. The mixture was evaporated, and the residual oil was purified by column chromatography over silica gel eluting with a mixture of 5% ammoniacal methanol and dichloromethane (9:91) to give the product as a colourless gum.

T.l.c. $SiO_2$:5% $NH_3$ in MeOH:DCM (10:90); Rf=0.30

MS: Found $MH^+$=299, 301; Required $MH^+$=299,301

NMR: δ($CDCl_3$) 8.58 (1H,d), 8.39 (1H,d), 7.80 (1H,t), 4.1–3.9 (2H,m), 3.80–3.70 (3H,m+s), 3.38–3.20 (2H,m), 2.10 (1H,brs), 1.95–1.76 (2H,m).

b) 1-[[5-[3-[2-(Dimethylamino)ethyl]-5-benzofuranyl]-3-pyridinyl]acetyl]-4-piperidinol dihydrochloride A degassed mixture of the intermediate from step (a) (282 mg), Intermediate 3 (220 mg), palladium tetrakis(triphenylphosphine) (86 mg), 2N aq. sodium carbonate (6.5 ml), and 1,2-dimethoxyethane (24 ml) was heated in a nitrogen atmosphere at reflux with stirring for 4 h. The mixture was treated with additional 2N aq. sodium carbonate (20 ml), extracted with ethyl acetate (3×20 ml), and the combined organic extracts were washed with brine (1×20 ml), dried, and evaporated to leave an oil. The oil was purified by column chromatography over silica gel eluting with a mixture of 5% ammoniacal methanol and dichloromethane (13:87) to give a colourless gum. The gum was dissolved in ethanol (5 ml), treated with 1.0M ethereal hydrogen chloride (3 ml), and this solution was evaporated to leave the product as a hygroscopic, white powder: m.p. 125°–130° C.

T.l.c. SiO$_2$:5% NH$_3$ in MeOH:DCM (13:87); Rf (free base)=0.40

MS: Found MH$^+$=408; Required MH$^+$=408

NMR: δ(CDCl$_3$) 10.65 (1H,brs), 9.18 (1H,d), 8.68 (1H,d), 8.60 (1H,brs), 8.35 (1H,brs), 8.04 (1H,brs), 7.8 (2H,brs), 4.05 (2H,s), 4.0–3.0 (9H,m), 2.88 (6H,s), 1.90–1.20 (4H,2× m).

EXAMPLE 5

1-[[5-[3-[2-(Dimethylamino)ethyl]-5-benzofuranyl]-3-pyridinyl]acetyl-4-methoxypiperidine oxalate (1:1)

a)
1-[(5-Bromo-3-pyridinyl)acetyl]-4-methoxypiperidine

A mixture of the 5-bromo-3-pyridine acetic acid (428 mg), 4-methoxypiperidine hydrochloride (300 mg), triethylamine (826 μl), diphenylphosphoryl azide (640 μl), and DMF (10 ml) was stirred at +23° for 5 h. The mixture was evaporated, and the residual yellow oil was purified by column chromatography over silica gel eluting with a mixture of 5% ammoniacal methanol and dichloromethane (5:95) to give the product as a colourless gum.

T.l.c. SiO$_2$:5% NH$_3$ in MeOH:DCM (5:95); Rf=0.30

MS: Found MH$^+$=313, 315; Required MH$^+$=313, 315

NMR: δ(CDCl$_3$) 8.57 (1H,d), 8.39 (1H,d), 7.80 (1H,t), 3.9–3.78 (1H,m), 3.75–3.6 (3H,m+s), 3.5–3.25 (6H,2×m+s), 1.9–1.5 (4H,2×m).

b) 1-[[5-[3-[2-(Dimethylamino)ethyl]-5-benzofuranyl]-3-pyridinyl]acetyl]-4 -methoxypiperidine oxalate (1:1)

A degassed mixture of the intermediate of step a) (443 mg), Intermediate 3 (330 mg), palladium tetrakis(triphenylphosphine) (64 mg), 2N aq. sodium carbonate (6.5 ml), and 1,2-dimethoxyethane (24 ml) was heated in a nitrogen atmosphere at reflux with stirring for 3 h. The mixture was treated with additional 2N aq. sodium carbonate (25 ml), extracted with ethyl acetate (3×25 ml), and the combined organic extracts were washed with brine (1×20 ml), dried, and evaporated to leave an oil. The oil was purified by column chromatography over silica gel eluting with a mixture of 5% ammoniacal methanol and dichloromethane (8:92) to give a colourless gum. The gum was dissolved in ethanol (3 ml), treated with a solution of oxalic acid (79 mg) in ethanol (1 ml), and this mixture was evaporated to leave the product as a hydgroscopic white foam: m.p. 70° (softens).

T.l.c. SiO$_2$:5% NH$_3$ in MeOH:DCM (8.92); Rf (free base)=0.30

MS: Found MH$^+$=422; Required MH$^+$=422

NMR: δ(CDCl$_3$) 8.88 (1H,d), 8.42 (1H,d), 8.10 (1H,d), 8.0+7.98 (2H,s+t), 7.54 (1H,d), 7.68 (1H,dd), 3.93–3.73 (4H,s+m), 3.5–3.05 (10H,2×m+s), 1.9–1.75 (2H,m), 1.5–1.25 (2H,m).

EXAMPLE 6

1-[[5-[3-[2-(Dimethylamino)ethyl]-5-benzofuranyl]-3-pyridinyl]acetyl]-4 methylsulphonyl)piperazine a) 1-[(5-Bromo-3-pyridinyl)acetyl]piperazine Diphenylphosphoryl azide (1.916 g) was added at −5° under nitrogen to a stirred solution of 3-bromo-5-pyridine acetic acid (754 mg), triethylamine (1.416 g) and piperazine (1.5 g) in DMF (50 ml). Stirring was continued for 17 h during which time the temperature was allowed to rise to +23°. Further diphenylphosphorylazide (0.383 g) was added at −5° and stirring continued at +23° for 6 h. the reaction mixture was evaporated and the orange residue purified by flash chromatography over silica gel (100 g). Elution with dichloromethane- ethanol-0.88 ammonia (100:8:1) gave a cream solid which was further purified by column chromatography over silica gel (75 g). Gradient elution with dichloromethane-ethanol-0.88 ammonia (150.8:1 100:8:1) gave the product as a light brown oil.

T.l.c. SiO$_2$; CH$_2$Cl$_2$:EtOH:0.88 NH$_3$ (100:8:1) Rf 0.24; u.v.

NMR: δ(CDCl$_3$) 8.58 (1H,d), 8.38 (1H,d), 7.8 (1H,t), 3.68 (2H,s), 3.62, 3.47 (4H,2×m), 2.9–2.8 (4H,m).

b) 1-[(5-Bromo-3-pyridinyl)acetyl]-4-(methylsulphonyl)piperazine

Methanesulphonyl chloride (0.15 ml) was added dropwise under nitrogen to a stirred solution of the piperazide of step (a) (275 mg) and triethylamine (0.54 ml) in dichloromethane (10 ml) at 0°. Stirring was continued at below 0° for 3.5 h and then at +23° for 3.5 h. Aqueous saturated sodium bicarbonate (25 ml) was added, the mixture separated, and the aqueous phase extracted with dichloromethane (5×15 ml). The combined, dried organic phases were evaporated to give an orange-brown residue (559 mg). This was purified by column chromatography over silica gel (30 g), eluting with dichloromethane-ethanol- 0.88 ammonia (200:8:1) to give the product as a cream powdery solid, m.p. 148°–150°.

T.l.c. SiO$_2$; CH$_2$Cl$_2$:EtOH:0.88 NH$_3$ (150:8:1) Rf 0.28; u.v., IPA

NMR: δ(CDCl$_3$) 8.60 (1H,d), 8.39 (1H,d), 7.79 (1H,t), 3.78 (2H,m), 3.71 (2H,s), 3.63 (2H,m), 3.22 (4H,m), 2.8 (3H,s).

c)
1-[[5-[3-[2-(Dimethylamino)ethyl]-5-benzofuranyl]-3-pyridinyl]acetyl]-4-(methylsulphonyl)piperazine The sulphamide of step (b) (278 mg), Intermediate 3 (180 mg), aqueous 2N sodium carbonate (3 ml), and DMF (25 ml) were stirred under nitrogen whilst nitrogen was bubbled through the mixture for 1 min. Tetrakis(triphenylphosphine)palladium (O) (36 mg) was added and the mixture stirred at reflux for 5 h. The cooled mixture was evaporated, aqueous 8% sodium carbonate (40 ml) was added, and the mixture extracted with ethyl acetate (6×30 ml). The combined, dried (MgSO$_4$) organic extracts were evaporated and the resultant light brown oil was purified by column chromatography over silica gel (50 g). Elution with dichloromethane-ethanol-0.88 ammonia (150:8:1) gave the product as a hygroscopic cream foam, m.p. 80°–85°.

T.l.c. SiO$_2$; CH$_2$Cl$_2$:EtOH:0.88 NH$_3$, (50:8:1) Rf 0.1; u.v., IPA

NMR: δ(CDCl$_3$) 8.80 (1H,d), 8.45 (1H,d), 7.83 (1H,t), 7.74 (1H,d), 7.6–7.45 (3H,m), 3.85–3.75 (4H,s+m), 3.7–3.63 (2H,m), 3.3–3.15 (4H,m), 2.9 (2H,½AA'BB'), 2.78 (3H,s), 2.66 (2H,½AA'BB'), 2.35 (6H,s).

EXAMPLE 7

4-[[5-[3-[2-(Dimethylamino)ethyl]-5-benzofuranyl]-3-pyridinyl]acetyl]morpholine dihydrochloride A degassed mixture of Intermediate 5 (8.00 g), Intermediate 2 (5.80 g), palladium tetrakis(triphenylphosphine) (300 mg), and xylene (400 ml) was heated at reflux under a nitrogen atmosphere with stirring for 20 h. The mixture was evaporated, and the dark residual oil was purified by column chromatography over silica gel eluting with a mixture of 5% ammoniacal methanol and dichloromethane (8:92→ 10:90) to give a colourless gum. The gum was dissolved in absolute ethanol (30 ml), and treated successively with 1.0M ethereal hydrogen chloride (50 ml), diethyl ether (100 ml), and methanol (5 ml) to give the product as a precipitated white powder, m.p. 248°–250°.

T.l.c. $SiO_2$:5% $NH_3$ in MeOH:DCM (8:92); Rf (free base)=0.20

Assay Found: C,58.14; H,6.08; N,8.47

$C_{23}H_{27}N_3O_3.2HCl.0.6H_2O$ requires: C,57.84; H,6.38; N,8.80

EXAMPLE 8

4-[[5-[3-[2-(Dimethylamino)ethyl]-5-benzofuranyl]-3-pyridinyl] acetyl]-acetidine oxalate (1:1)

a) 1-[(5-Bromo-3-pyridinyl)acetyl]-acetidine

Azetidinium tetrafluoroborate (400 mg) was added to a cold (0°–5°), stirring solution of 5-bromo-3-pyridine acetic acid (597 mg), triethylamine (1.15 ml), and diphenylphosphoryl azide (890 µl) in dimethylformamide (10 ml). The mixture was stirred at +23° for 20 h, evaporated, and the residual oil was purified by column chromatography over silica gel (Merck 9385) eluting with a mixture of 5% ammoniacal methanol and dichloromethane (5:95) to give the product as a crystalline white solid, m.p. 92°–93°.

T.l.c. $SiO_2$:5% $NH_3$ in MeOH:DCM (5:95): $UV_{254}$/IPA: RF=0.30

Assay Found: C,46.09; H,4.24; N,11.05

$C_{10}H_{11}BrN_2O$ requires: C,46.10; H,4.49; N,10.75 b) 1-[[3-Pyridinyl-5-(trimethylstannyl)]acetyl]-acetidine

A degassed mixture of the amide of step (a) (300 mg), hexamethyldistannane (490 µl), palladium tetrakis(triphenylphosphine) (68 mg), and xylene (20 ml) was heated at reflux under a nitrogen atmosphere with stirring for 4 h. Additional palladium tetrakis(triphenylphosphine) (50 mg) was added, and heating was continued for a further 16 h. The mixture was evaporated, and the residual dark oil was purified by column chromatography over silica gel (Merck 9385) eluting with a mixture of 5% ammoniacal methanol and dichloromethane (4:96) to give the product as a colourless oil.

T.l.c. $SiO_2$:5% $NH_3$ in MeOH:DCM (4:96): $UV_{254}$/IPA: RF=0.30

N.m.r.($CDCl_3$; δ) 8.50 (1H,d), 8.40 (1H,d), 7.6 (1H,t), 4.20 (2H,t), 4.05 (2H,t), 3.4 (2H,s), 2.29 (2H,m), 0.35 (9H,s).

c) 1-[[5-[3-[2-(Dimethylamino)ethyl]-5-benzofuranyl]-3-pyridinyl]acetyl]-azetidine oxalate (1:1)

A mixture of the stannane of step (b) (210 mg), Intermediate 2 (170 mg), palladium tetrakis(triphenylphosphine) (35 mg), and xylene (20 ml) was heated at reflux with stirring under a nitrogen atmosphere for 4 h. The solvent was evaporated, and the residual dark oil was purified by column chromatography over silica gel (Merck 9385) eluting with a mixture of 5% ammoniacal methanol and dichloromethane (8:92) to give a colourless gum. The gum was dissolved in ethanol (2 ml), treated with oxalic acid (32 mg), and the solution was evaporated to give the product as a white foam, m.p. 115° (softens).

T.l.c. $SiO_2$:5% $NH_3$ in MeOH:DCM (8:92): $UV_{254}$/IPA: RF (free base)=0.30

M.S. Found $MH^+$=364; Required $MH^+$=364

N.m.r.($CDCl_3$; δ) 8.86 (1H,d), 8.44 (1H,d), 8.09 (1H,t), 8.00 (2H,d+s), 7.73 (1H,d), 7.68 (1H,d), 4.28 (2H,t), 3.89 (2H,t), 3.56 (2H,d), 3.36 (2H,m), 3.13 (2H,m), 2.82 (6H,s), 2.24 (2H,m).

EXAMPLE 9

4-[[5-[3-[2-(Dimethylamino)ethyl]-5-benzofuranyl]-3-pyridinyl]acetyl]morpholine dihydrochloride A degassed mixture of Intermediate 5 (28.55 g), Intermediate 2 (20.81 g), palladium tetrakis(triphenylphosphine) (1g), and xylenes (1.4 L) was heated at reflux under a nitrogen atmosphere with stirring for 1.5 hours. The cooled reaction mixture was diluted with methanol (250 cm³), clarified and evaporated to give a dark residual oil, which was purified by column chromatography (silica gel) eluting with a mixture 10% ammoniacal methanol and dichloromethane (8:92) to give a gum. The gum was dissolved in warm industrial methylated spirits (100 cm³), clarified, diluted with further industrial methylated spirits (56.5 cm³) and treated with concentrated hydrochloric acid (7.67 cm³). After seeding and refrigeration the product was isolated as a white crystalline solid, mp., t.l.c. and NMR as found for the product of Example 7.

EXAMPLE 10

4-[[5-[3-[2-(Dimethylamino)ethyl]-5-benzofuranyl]-3-pyridinyl]acetyl]morpholine dihydrochloride A degassed mixture of Intermediate 5 (0.757 g), Intermediate 6 (0.61 g), lithium chloride (0.252 g), palladium tetrakis(triphenylphosphine) (0.046 g), and 2,6-di-t-butyl-4-methylphenol (2 crystals) in dry 1,4-dioxan (9 cm³) was heated at reflux under a nitrogen atmosphere with stirring for 21 hours. The cooled reaction mixture was diluted with methanol, clarified and evaporated to give an oil. Inorganic salts were removed by an extractive isolation involving water, 5M aqueous sodium hydroxide solution, ethyl acetate and dichloromethane. Evaporation of the organic extracts produced an oil which was purified by column chromatography (silica gel) eluting with a mixture of 10% ammoniacal methanol and dichloromethane (8:92) to give a gum. The gum was dissolved in warm methanol (2.8 cm³) and treated with 1M ethereal HCl (2.8 cm³) to give the product as a white crystalline solid, m.p., t.l.c. and NMR as found for the product of Example 7.

EXAMPLE 11

4-[[5-[3-[2-(Methylamino)ethyl]-5-benzofuranyl]-3-pyridinyl]acetyl]morpholine dihydrochloride The compound of Example 11 was prepared using methods analogous to those described in Examples 1 to 10.

T.l.c. $SiO_2$:5% $NH_3$ in MeOH:DCM (1:9); $UV_{254}$/IPA Rf (free base)=0.25

M.S. Found: $MH^+$=380; Required $MH^+$=380 (free base)

Assay Found: C,55.1; H,6.6; N,8.6

$C_{22}H_{25}N_3O_3 \cdot 2HCl \cdot 1.5H_2O$ requires: C,55.1; H,6.3; N,8.8

The following examples illustrate pharmaceutical formulations according to the invention containing 1-[[5-[3-[2-(dimethylamino)ethyl]-5-benzofuranyl]-3-pyridinyl]acetyl]piperidine; 1-[[5-[3-[2-(dimethylamino)ethyl]-5-benzofuranyl]-3-pyridinyl]acetyl]pyrrolidine; or 4-[[5-[3-[2-(dimethylamino)ethyl]-5-benzofuranyl]-3-pyridinyl]acetyl]morpholine (free base of dihydrochloride salt) as the active ingredient. Other compounds of the invention may be formulated in a similar manner.

TABLETS FOR ORAL ADMINISTRATION

A. Direct Compression

| 1. | mg/tablet |
| --- | --- |
| Active ingredient | 49 |
| Magnesium Stearate BP | 0.65 |
| Anhydrous Lactose | 81 |

The active ingredient is sieved and blended with the anhydrous lactose and magnesium stearate. The resultant mix is compressed into tablets using a tablet machine fitted with appropriately sized concave punches.

| 2. | mg/tablet |
| --- | --- |
| Active ingredient | 49 |
| Magnesium Stearate BP | 0.7 |
| Microcrystalline cellulose NF | 91 |

The active ingredient is sieved and blended with the microcrystalline cellulose and magnesium stearate. The resultant mix is compressed into tablets using a tablet machine fitted with appropriately sized concave punches.

B. Wet Granulation

| | mg/tablet |
| --- | --- |
| Active Ingredient | 7.0 |
| Lactose BP | 146.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using suitable diameter punches.

Tablets of other strengths may be prepared by altering the ratio of active ingredient to lactose or the compression weight and using punches to suit.

The tablets may be film coated with suitable film-forming materials, such as hydroxypropyl methylcellulose, using standard techniques. Alternatively the tablets may be sugar coated, or enteric coated.

FILM COATED TABLETS

| Tablet cores | Unit formula (mg/tablet) |
| --- | --- |

| | |
| --- | --- |
| Active ingredient/lactose granule* | 280.0 |
| Microcrystalline cellulose Ph Eur | 15.5 |
| Croscarmellose Sodium USNF | 3.0 |
| Magnesium Stearate Ph Eur | 1.25–1.75 |

| *Active ingredient/lactose granule | mg |
| --- | --- |
| Active ingredient | 140.0 |
| Lactose Ph Eur 170 mesh | 140.0 |
| Purified water Ph Eur | qs + |

| Coating Suspension | % w/w |
| --- | --- |
| Hydroxypropyl methylcellulose Ph Eur | 10.0 |
| Opaspray white # | 5.0 |
| Purified water Ph Eur to | 100.0++ |

+The water does not appear in the final product. Typical range 100–140 g per kg of blend.
++The water does not appear in the final product. The maximum theoretical weight of solids applied during coating is 11 mg/tablet.
Opaspray white is a proprietory film coating suspension, obtainable from Colorcon Ltd, UK, which contains hydroxypropyl methylcellulose and titanium dioxide.

The active ingredient and lactose are mixed together and granulated by the addition of purified water. The granules obtained after mixing are dried and passed through a screen, and the resulting granules are then mixed with the other tablet core excipients. The mix is compressed into tablets. The tablets are then film coated using the coating suspension in conventional film coating equipment.

| | mg/tablet |
| --- | --- |
| Active ingredient | 140.0 mg |
| Sodium bicarbonate | 656.4 mg |
| Monosodium citrate anhydrous | 659.5 mg |
| Aspartame | 40.0 mg |
| Polyvinylpyrrolidone | 32.0 mg |
| Sodium benzoate | 48.0 mg |
| Orange flavour | 16.0 mg |
| Lemon flavour | 8.0 mg |
| Absolute alcohol for granulation | |

The active ingredient, anhydrous monosodium citrate, sodium bicarbonate and aspartame are mixed together and granulated by the addition of a solution of the polyvinylpyrrolidone in the alcohol. The granules obtained after mixing are dried and passed through a screen, and the resulting granules are then mixed with the sodium benzoate and flavourings. The granulated material is compressed into tablets using an machine fitted with 20 mm punches.

A rotary machine fitted with 20 mm punches may also be used for tabletting.

LIQUID AND CAPSULE FORMULATIONS FOR ORAL ADMINISTRATION

Liquid formulations are prepared by slow addition of active ingredient into the other ingredients at 35°–50° C. with constant mixing (amounts are given as percentage w/w).

| Example | A | B |
| --- | --- | --- |
| Active ingredient | 18.2 | 18.2 |
| Oleic acid | 60.985 | 68.485 |
| Polyethylene glycol 600 | 7.3 | 7.3 |
| Propylene glycol | 6.0 | 6.0 |
| Polysorbate 80 | 7.5 | — |
| Ascorbyl palmitate | 0.015 | 0.015 |

The liquid formulations are filed into hard gelatin capsules, each capsule containing 25 mg of active ingredient.

CAPSULES

|  | mg/capsule |
| --- | --- |
| Active ingredient | 49.0 |
| *Starch 1500 | 150.0 |
| Magnesium Stearate BP | 1.0 |
| Fill weight | 200.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

SYRUP

| Sucrose Free Presentation | mg/5 ml dose |
| --- | --- |
| Active ingredient | 49.0 |
| Hydroxypropylmethylcellulose USP (viscosity type 4000) | 22.5 |
| Buffer | |
| Flavour | |
| Colour | as required |
| Preservative | |
| Sweetener | |
| Purified water BP to | 5.0 ml |

The hydroxypropylmyethylcellulose is dispersed in hot water, cooled and then mixed with an aqueous solution containing the active ingredient and the other components of the formulation. The resultant solution is adjusted to volume and mixed. The syrup is clarified by filtration.

SUSPENSION

|  | mg/5 ml dose |
| --- | --- |
| Active ingredient | 49.0 |
| Aluminium monostearate | 75.0 |
| Sweetening agent | |
| Flavour | |
| Colour | as required |
| Fractionated coconut oil to | 5.0 ml |

The aluminium monostearate is dispersed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

SUB-LINGUAL TABLET

|  | (mg/tablet) |
| --- | --- |
| Active ingredient/lactose granule* | 49.0 |
| Compressible sugar NF | 50.5 |
| Magnesium Stearate BP | 0.5 |
| Compression Weight | 100.0 |

The active ingredient is sieved through a suitable sieve, blended with the excipients and compressed using suitable punches. Tablets of other strengths may be prepared by altering either the ratio of active ingredient to excipients or the compression weight and using punches to suit.

SUPPOSITORY FOR RECTAL ADMINISTRATION

| Active ingredient | 49.0 mg |
| --- | --- |
| *Witepsol W32 | 1.0 g |

*A propietary grade of Adeps Solidus Ph Eur

A suspension of the active ingredient in molten Witepsol is prepared and filled using suitable machinery, into 1 g size suppository moulds.

INJECTION FOR SUBCUTANEOUS ADMINISTRATION

|  | mg/ml |
| --- | --- |
| Active ingredient | 0.896 |
| Sodium Chloride Intravenous Infusion, BP, 0.9% w/v | to 1 ml |
| Batch size | 2500 ml |

The active ingredient is dissolved in a portion of the Sodium Chloride Intravenous Infusion, the solution made to volume with the Sodium Chloride Intravenous Infusion, and the solution thoroughly mixed. The solution is filled into clear, Type 1, glass 1 ml ampoules and sealed under a nitrogen headspace by fusion of the glass. The ampoules are sterilised by autoclaving at 121° for not less than 15 minutes.

FOR INHALATION

Inhalation Cartridges

|  | mg/cartridge |
| --- | --- |
| Active ingredient (micronised) | 0.56 |
| Lactose BP | 25.00 |

The active ingredient is micronised in a fluid energy mill to a fine particle size range prior to blending with normal tabletting grade lactose in a high energy mixer. The powder blend is filled into No 3 hard gelatin capsules on a suitable encapsulating machine. The contents of the cartridges are administered using a powder inhaler such as the Glaxo Rotahaler.

Metered Dose Pressurised Aerosol

| Suspension Aerosol | mg/metered dose | Per can |
| --- | --- | --- |
| Active ingredient (micronised) | 0.280 | 73.92 mg |
| Oleic Acid BP | 0.020 | 5.28 mg |
| Trichlorofluoromethane BP | 23.64 | 5.67 g |
| Dichlorodifluoromethane BP | 61.25 | 14.70 g |

The active ingredient in micronised in a fluid energy mill to a fine particle size range. The oleic acid is mixed with the trichloromethane at a temperature of 10°– 15° and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

NASAL SPRAY

|  | % w/v |
|---|---|
| Active ingredient | 7.0 |
| Sodium Chloride BP | |
| Purified Water BP to | 100 |
| Shot Weight | 100 mg (equivalent to 7 mg active ingredient) |

The active ingredient and sodium chloride are dissolved in a portion of the water, the solution made to volume with the water and the solution thoroughly mixed.

The pH may be adjusted, using acid or alkali, to that of optimum stability and/or to facilitate solution of the active ingredient. Alternatively, suitable buffer salts may be used.

We claim:

1. A compound of formula (I)

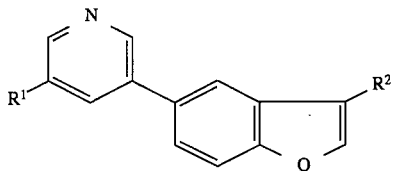

wherein $R^1$ is —$CH_2CONR^3R^4$;

$R^2$ is —$CH_2CH_2NR^5R^6$;

$R^3$ and $R^4$, together with the N-atom to which they are attached form a saturated 4- to 7-membered ring of formula

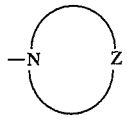

where

Z is a group of formula —$CR^7R^8$—, —O— or —$NR^9$—;

$R^5$ and $R^6$, which may be the same or different, are hydrogen or $C_{1-3}$alkyl;

$R^7$ and $R^8$, which may be the same or different, are hydrogen, hydroxy or $C_{1-3}$ alkoxy;

$R^9$ is —$SO_2R^{10}$, —$COR^{10}$ or —$COOR^{10}$;

$R^{10}$ is $C_{1-3}$alkyl;

and pharmaceutically acceptable salts and solvates thereof.

2. A compound as claimed in claim 1 wherein $R^3$ and $R^4$, together with the N-atom to which they are attached, form an azetidine, pyrrolidine, piperidine, hexamethyleneimine, piperazine or morpholine ring.

3. A compound as claimed in claim 1 wherein $R^1$ is

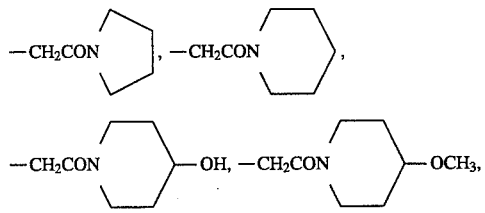

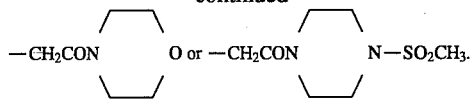

4. A compound as claimed in claim 1 wherein $R^5$ and $R^6$ are both methyl.

5. A compound selected from: 1-[[5-[3-[2-(Dimethylamino)ethyl]-5-benzofuranyl]-3-pyridinyl]acetyl]piperidine; 1-[[5-[3-[2-(Dimethylamino)ethyl]-5-benzofuranyl]-3-pyridinyl]acetyl]pyrrolidine; 4-[[5-[3-[2-(Dimethylamino)ethyl]-5-benzofuranyl]-3-pyridinyl]acetyl]morpholine; 1-[[5-[3-[2-(Dimethylamino)ethyl]-5-benzofuranyl]-3-pyridinyl]acetyl]-4 -piperidinol; 1-[[5-[3-[2-(Dimethylamino)ethyl]-5-benzofuranyl]-3-pyridinyl]acetyl]-4 -methoxypiperidine; 1-[[5-[3-[2-(Dimethylamino)ethyl]-5-benzofuranyl]-3-pyridinyl]acetyl]-4 methylsulphonyl)piperazine; 1-[[5-[3-[2-(Dimethylamino)ethyl]-5-benzofuranyl]-3-pyridinyl]acetyl]-azetidine; 4-[[5-[3-[2-(Methylamino)ethyl]-5-benzofuranyl]-3-pyridinyl]acetyl-acetyl] morpholine;

and pharmaceutically acceptable salts and solvates thereof.

6. 1-[[5-[3-[2-(Dimethylamino)ethyl]-5-benzofuranyl]-3-pyridinyl]acetyl]piperidine and pharmaceutically acceptable salts and solvates thereof.

7. 1-[[5-[3-[2-(Dimethylamino)ethyl]-5-benzofuranyl]-3-pyridinyl]acetyl] pyrrolidine and pharmaceutically acceptable salts and solvates thereof as claimed in claim 5.

8. 4-[[5-[3-[2-(Dimethylamino)ethyl]-5-benzofuranyl]-3-pyridinyl]acetyl]morpholine and pharmaceutically acceptable salts and solvates thereof as claimed in claim 5.

9. A pharmaceutical composition which comprises as active ingredient a compound of formula (I) as defined in claim 1 or a pharmaceutically acceptable salt or solvate thereof together with one or more pharmaceutically acceptable carriers or excipients.

10. A pharmaceutical composition as claimed in claim 9 adapted for oral, parenteral, rectal or intranasal administration.

11. A pharmaceutical composition as claimed in claim 9 which is formulated in unit dosage from comprising 0.1 to 200 mg of active ingredient.

12. A pharmaceutical composition according to claim 9 wherein the compound is 1-[[5-[3-[2-(dimethylamino)ethyl] -5 -benzofuranyl]-3-pyridinyl]acetyl]piperidine or a pharmaceutically acceptable salt or solvate thereof.

13. A pharmaceutical composition according to claim 9 wherein the compound is b 1-[[5-[3-[2-(dimethylamino)ethyl]-5 -benzofuranyl]-3-pyridinyl]acetyl]-pyrrolidine or a pharmaceutically acceptable salt or solvate thereof.

14. A pharmaceutical composition according to claim 9 wherein the compound is 4-[[5-[3-[2-(dimethylamino)ethyl] -5 -benzofuranyl]-3-pyridinyl]acetyl]-morpholine or a pharmaceutically acceptable salt or solvate thereof.

15. A method for the treatment of a mammal, including man, comprising administration of an effective amount of a compound of formula (I) as defined in claim 1 for the treatment of conditions associated with cephalic pain and in alleviating the symptoms associated therewith.

16. A method of treatment as claimed in claim 15 for treating a human susceptible to or suffering from migraine, cluster headache, chronic paroxysmal hemicrania, headache associated with vascular disorders, tension-type headache, headache associated with substances or their withdrawal (e.g. drug withdrawal), trigeminal neuralgia and headache associated with meningeal irritation.

17. A method of treatment according to claim 15 wherein the compound of formula (I) is 1-[[5-[3-[2-(dimethylamino- )ethyl]-5-benzofuranyl]-3-pyridinyl]acetyl]piperidine or a pharmaceutically acceptable salt or solvate thereof.

18. A method of treatment according to claim 15 wherein the compound of formula (I) is 1-[[5-[3-[2-(dimethylamino)ethyl]-5-benzofuranyl]-3-pyridinyl]acetyl]pyrrolidine or a pharmaceutically acceptable salt or solvate thereof.

19. A method of treatment according to claim 15 wherein the compound of formula (I) is 4-[[5-[3-[2-(dimethylamino)ethyl]-5-benzofuranyl]-3-pyridinyl]acetyl]-morpholine or a pharmaceutically acceptable salt or solvate thereof.

* * * * *